United States Patent [19]
Poole et al.

[11] Patent Number: 5,278,626
[45] Date of Patent: Jan. 11, 1994

[54] NON-VOLATILE RESIDUE SYSTEM FOR MONITORING IMPURITIES IN A LIQUID

[75] Inventors: Trent A. Poole, South Amherst; Robert E. Carter, Arlington, both of Mass.

[73] Assignee: Amherst Process Instruments, Inc., Hadley, Mass.

[21] Appl. No.: 755,054

[22] Filed: Sep. 5, 1991

[51] Int. Cl.$^5$ .................... G01N 1/10; G01N 15/14
[52] U.S. Cl. .................... 356/36; 356/37; 356/335; 356/336; 356/337; 436/36; 422/73
[58] Field of Search ............ 356/36, 37, 335, 336, 356/337; 422/73, 110, 112, 115; 436/36

[56] References Cited

U.S. PATENT DOCUMENTS

3,941,479  3/1976  Whitehead ..................... 356/335
5,098,657  4/1992  Blackford et al. ............... 422/73

Primary Examiner—Vincent P. McGraw
Assistant Examiner—LaCharles Keesee
Attorney, Agent, or Firm—Wolf, Greenfield & Sacks

[57] ABSTRACT

A system for monitoring and analyzing impurities in a liquid by analyzing the non-volatile residue of droplets of the liquid includes a droplet generator for generating a stream of droplets of the liquid, a droplet inspection unit, a drop-on-demand unit for removing selected droplets from the stream of droplets, a heat exchanger for drying the droplets to provide non-volatile residue particles, and a particle size measurement unit. The droplet inspection unit determines the diameters of the droplets. A feedback arrangement from the droplet inspection unit controls droplet diameter by varying the droplet generation rate. The drop-on-demand unit removes a selected fraction of droplets from the droplet stream so as to reduce vapor loading in the heat exchanger and prevent agglomeration of droplets. The heat exchanger includes a first section for gradually increasing the temperature of the stream of droplets and a second section for maintaining the stream of droplets at the boiling temperature of the liquid. A vortex shedder can be used at the inlet to the heat exchanger to enhance heat transfer to the stream of droplets. The system can include an instrument for analyzing the composition of the particles.

32 Claims, 4 Drawing Sheets

NON-VOLATILE RESIDUE SYSTEM FOR MONITORING IMPURITIES IN A LIQUID

FIELD OF THE INVENTION

This invention relates to systems for monitoring and analyzing impurities in a liquid and, more particularly, to methods and apparatus for analyzing the non-volatile residue of droplets of the liquid with high accuracy and high resolution.

BACKGROUND OF THE INVENTION

Ultrapure liquids are used in various industrial processes such as semiconductor wafer fabrication. Liquids such acetone, freon, alcohol, xylene, water, and the like may be used in process steps such as cleaning, rinsing, etc. Although the liquids are ultrapure, they contain traces of impurities or contaminants. Contaminants in the liquids produce a residue on the semiconductor wafers after drying. The microminiature devices on the semiconductor wafers may be rendered defective by even a slight residue from the liquids used. Thus, it is desirable to monitor impurity levels in the liquids used. Impurity concentrations on the order of tens of parts per billion may be sufficient to cause defects in semiconductor wafers. The measurement of such low impurity concentrations has been extremely difficult.

A technique for measurement of sub parts per million concentrations of impurities in liquids is disclosed in U.S. Pat. No. 4,794,086, issued Dec. 27, 1988 to Kasper et al. The disclosed technique involves the dispersion of the liquid into droplets in a gas stream The droplets evaporate in the gas stream leaving residue particles having diameters that depend on the impurity level. The sizes of the particles are analyzed using a light scattering particle spectrometer, a condensation nuclei counter or an aerodynamic particle sizer. The concentration by volume of the impurities is calculated from the droplet diameter and the particle diameter. Aerodynamic particle sizing systems are disclosed in U.S. Pat. No. 3,854,321 issued Dec. 17, 1974 to Dahneke; U.S. Pat. No. 4,895,034 issued Jan. 23, 1990 to Poole; U.S. Pat. No. 4,917,494 issued Apr. 17, 1990 to Poole et al; and U.S. Pat. No. 4,938,592 issued Jul. 3, 1990 to Poole et al. A technique for measuring impurity concentrations in a liquid employing a condensation nuclei counter is disclosed in U.S. Pat. No. 4,761,074, issued Aug. 2, 1988 to Kohsaka et al.

The prior art techniques for monitoring impurities in ultrapure liquids have had one or more disadvantages which have resulted in poor accuracy and poor resolution. In particular, the non-volatile residue technique described above requires highly accurate measurement of both droplets and particles. Such measurement techniques have not been known in the prior art, since techniques for controlling droplet generation have not been developed. Furthermore, prior art systems for monitoring impurities in ultrapure liquids have not been suitable for use on a continuous basis in a production environment.

It is a general object of the present invention to provide improved methods and apparatus for monitoring impurities in liquids.

It is another object of the present invention to provide methods and apparatus for monitoring impurity levels in liquids with high accuracy and high resolution.

It is yet another object of the present invention to provide methods and apparatus for monitoring impurities in liquids by analyzing the non-volatile residue of single droplets of the liquid.

It is a further object of the present invention to provide a non-volatile residue system having accurate control over droplet generation.

It is still another object of the present invention to provide methods and apparatus for monitoring impurities in a liquid on a continuous basis in a production environment.

It is a further object of the present invention to provide methods and apparatus for monitoring impurity concentration and impurity composition in a liquid.

SUMMARY OF THE INVENTION

According to the present invention, these and other objects and advantages are achieved in methods and apparatus for monitoring impurities in a liquid by analyzing the non-volatile residue of droplets of the liquid with high accuracy and high resolution.

In accordance with a first aspect of the invention, a system for monitoring impurities in a liquid comprises means for generating a stream of droplets of the liquid, means for removing selected droplets from the stream of droplets, means for drying the stream of droplets after removal of the selected droplets to provide non-volatile residue particles, and means for analyzing the non-volatile residue particles to provide an indication of the impurities in the liquid.

The means for removing selected droplets preferably includes means for charging the selected droplets with an electrical charge to provide charged droplets and means for deflecting the charged droplets from the stream of droplets with an electric field. The means for charging preferably comprises a charging electrode positioned adjacent to the stream of droplets and means for applying a charging voltage to the charging electrode. The means for applying a charging voltage includes means for pulsing the charging voltage to zero volts to permit passage of non-selected droplets. The means for deflecting the charged droplets preferably comprises deflection electrodes positioned downstream of the charging electrode and means for applying a deflection voltage between the deflection electrodes. By periodically removing a predetermined fraction of the droplets, the spacing between droplets in the droplet stream is increased.

According to another aspect of the invention, a system for monitoring impurities in a liquid comprises means for generating a stream of droplets of the liquid, including a nozzle for emitting the stream of droplets and means for vibrating the nozzle at a droplet rate, means for inspecting the stream of droplets and determining a droplet diameter, feedback means responsive to the droplet diameter for varying the droplet rate when the droplet diameter is outside a predetermined range such that the droplet diameter is maintained within the predetermined range, means for drying the droplets to provide non-volatile residue particles, and means for analyzing the non-volatile residue particles to provide an indication of the impurities in the liquid.

In a first embodiment, the means for inspecting the stream of droplets comprises means for illuminating the stream of droplets with a light beam and means for detecting variations in the light beam caused by the droplets. The means for detecting can comprise a photodiode. In a second embodiment, the means for inspecting the stream of droplets comprises means for illuminating the stream of droplets, a camera for obtaining an image of the stream of droplets and means for analyzing the image to determine the diameter of the droplets. The means for vibrating the nozzle typically comprises a piezoelectric crystal attached to the nozzle and means for energizing the piezoelectric crystal at the droplet rate.

According to a further feature of the invention, a system for monitoring impurities in a liquid comprises means for generating a stream of droplets of the liquid, means for drying the droplets to provide non-volatile residue particles, the means for drying the droplets comprising a heat exchanger including a first section for gradually heating the droplets to a predetermined temperature and a second section for maintaining the droplets at the predetermined temperature, and means for analyzing the non-volatile residue particles to provide an indication of the impurities in the liquid.

The heat exchanger preferably includes a thermally-conductive heat exchanger tube extending through the first and second sections and a heater disposed around the heat exchanger tube in the second section. The first section has a log mean temperature profile, and the section has a constant temperature profile.

According to a further feature of the invention, the heat exchanger can include a vortex shedder at the inlet of the heat exchanger tube for producing turbulence along the inside wall of the heater exchanger tube to thereby improve heat transfer to the stream of droplets.

According to yet another aspect of the invention, a system for monitoring impurities in a liquid comprises means for generating a stream of droplets of the liquid, means for drying the droplets to provide non-residue particles, means for measuring the diameters of the non-volatile residue particles to provide an indication of the volume concentration of impurities in the liquid and means for analyzing the composition of the non-volatile residue particles to provide an indication of the composition of the impurities in the liquid. Typically, the means for measuring the diameters of the particles comprises an aerodynamic particle sizing system, and the means for analyzing the composition of the particles comprises a spectrometer.

BRIEF DESCRIPTION OF THE DRAWINGS

For a better understanding of the present invention, together with other and further objects, advantages and capabilities thereof, reference is made to the accompanying drawings which are incorporated herein by reference and in which.

DETAILED DESCRIPTION OF THE INVENTION

Figure 1A:
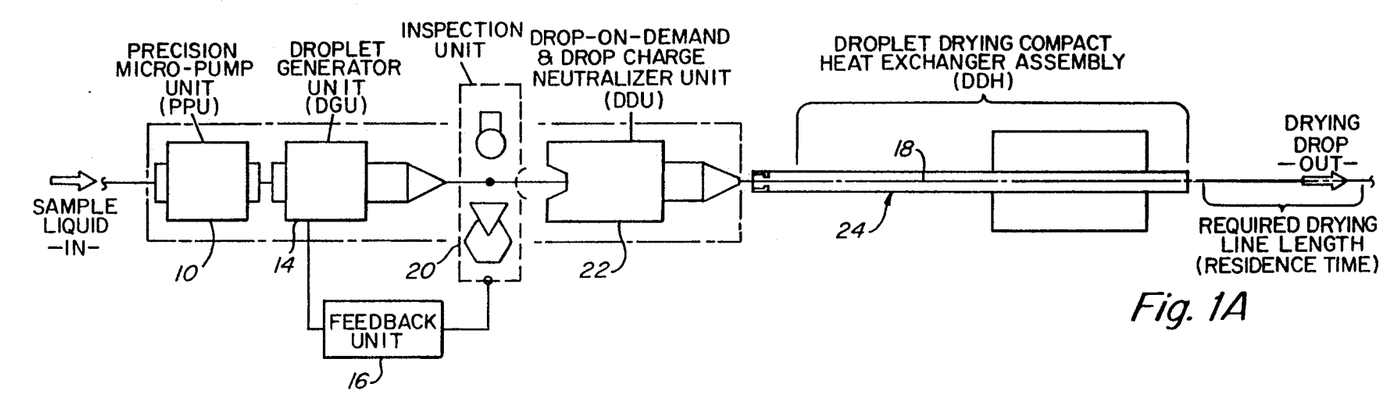
FIGS. 1A and 1B are block diagrams of a non-volatile residue system in accordance with the present invention.
Figure 1B:
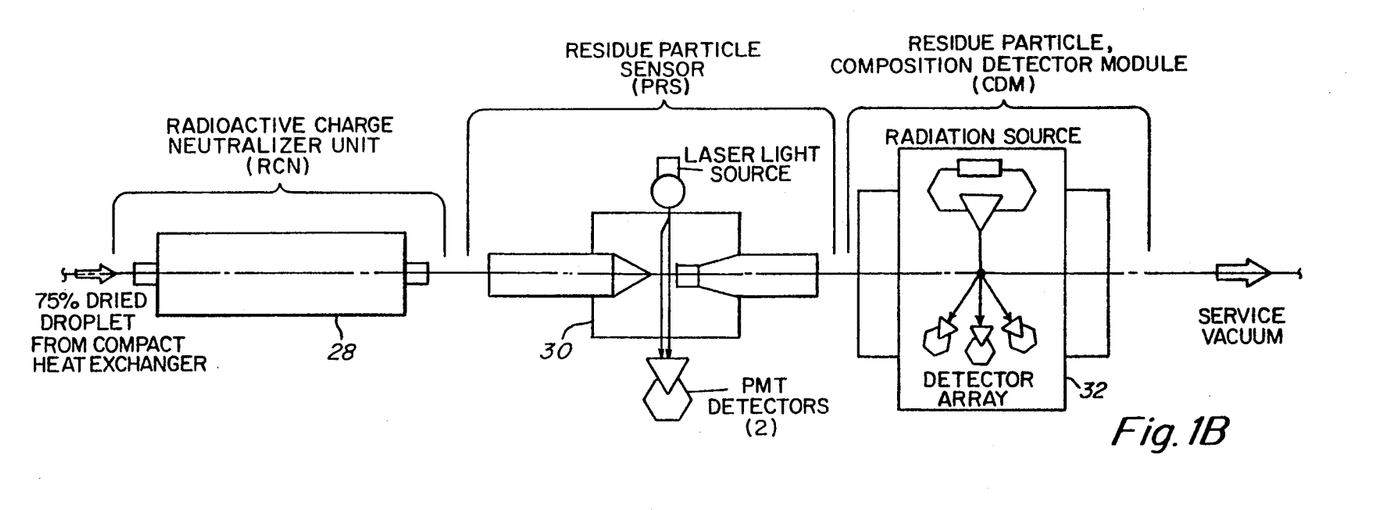

A block diagram of a non-volatile residue system in accordance with the present invention is shown in FIGS. 1A and 1B. The system continuously samples a process line or slipstream to obtain a liquid sample. The liquid sample is formed into a stream of droplets, and the droplets are dried to form non-volatile residue particles. The particles are supplied to a particle size measurement system and are measured. The particle size measurement system is used to calculate volume concentration of impurities in the sample. Optionally, the composition of the particles is analyzed. The system is capable of accurately measuring impurity concentrations of a few parts per billion in the liquid sample. The system operates continuously and automatically in a production environment.

Referring now to FIG. 1A, a liquid sample from a process line or slipstream is input to a precision micropump 10. The liquid is typically water, acetone, freon, alcohol or xylene, but is not limited to these liquids. The liquid sample is provided by the micropump 10 to a droplet generator 14 at a constant flow rate. The purpose of the droplet generator 14 is to convert the liquid sample into a precisely controlled stream of monodispersed droplets. The droplet stream is a stream of single droplets having a controlled size and preferably having a spherical shape. The stream of droplets travels along a longitudinal axis 18 of the system. The droplets preferably have a predetermined diameter in the range of about 55 micrometers to 150 micrometers. In a typical example, droplets with a diameter of 100 micrometers are generated. The droplets are typically generated by droplet generator 14 at a rate in the range of about 6000 to 12,000 droplets per second. As discussed below, the droplet size is dependent on the droplet generation rate. Thus, according to an important feature of the invention, the droplet size is controlled by varying the droplet generation rate. In accordance with another feature of the invention, the droplet generator 14 operates at a relatively high flow rate of about 0.3 to 0.6 cubic centimeters per minute and operates without a reservoir. Thus, the system provides a real time indication of the level of impurities in the process line or slipstream.

The stream of droplets generated by droplet generator 14 passes through a droplet inspection unit 20. The droplet inspection unit 20 includes a light source for illuminating the droplet stream and a photodiode or camera for inspecting the droplets as to size and shape. As discussed below, the droplet inspection unit 20 is used in a feedback system to control droplet generation.

The droplet stream, after passing through inspection unit 20, is input to a drop-on-demand unit 22. The function of the drop-on-demand unit 22 is to remove droplets from the droplet stream to reduce the droplet rate and thereby increase the separation between droplets in the droplet stream. Thus, for example, the droplet rate can be reduced from 10,000 droplets per second to 500 droplets per second. The droplet size is not altered by the drop-on-demand unit 22. The drop-on-demand unit is discussed in detail below.

The droplet stream is supplied from drop-on-demand unit 22 to a heat exchanger 24. The purpose of the heat exchanger 24 is to heat the droplet stream sufficiently to cause evaporation of the liquid from the droplet before each droplet reaches the particle size measurement unit. As each droplet evaporates, impurities in the droplet coalesce to form a particle. The size of the particle relative to the size of the droplet is representative of the volume concentration of impurities in the liquid sample. The droplets are preferably heated gradually to the boiling point of the liquid in the sample and then maintained at an elevated temperature until complete drying has occurred. The construction and operation of the heat exchanger are described below. The output of the heat exchanger 24 is a stream of partially dried droplets. The droplets continue to dry in the heated transport air.

The partially dried droplets are input to a charge neutralizer 28, as shown in FIG. 1B. The purpose of the charge neutralizer 28 is to eliminate or reduce static charge on the partially dried droplets. In a preferred embodiment, the charge neutralizer 28 comprises a model P-2021SS air line ionizer available from NRD, Inc. The charge neutralizer 28 can be omitted from the non-volatile residue system when droplet charging is not a problem.

The fully dried particles are input to a high resolution, submicron, aerodynamic particle sizer 30. The tube line length between heater exchanger 24 and particle sizer 30 is sufficient to permit complete drying of the particles before they reach particle sizer 30. The droplets continue drying in the heated air as they are transported from heat exchanger 24 to particle sizer 30. At the input to particle sizer 30, the transport air typically has a temperature of about 80° F. The particle sizer 30 can be a time-of-flight particle size measurement system as described in the aforementioned U.S. Pat. Nos. 3,854,321; 4,895,034; 4,917,494; and 4,938,592. A preferred particle sizing system is an Aerosizer, Mach II, available from Amherst Process Instruments, Inc.

In some instances, it is desirable to determine impurity composition as well as impurity concentration in the liquid sample. The non-volatile residue system of the present invention can include a composition analyzer 32 which receives the particle stream from particle sizer 30. The composition analyzer 32 can be a spectrograph such as a Model 100S Spectrograph available from American Holograph. Alternatively, the composition analyzer 32 can utilize X-ray spectroscopy, light signature analysis, or any other suitable analysis instrument.

Figure 2:
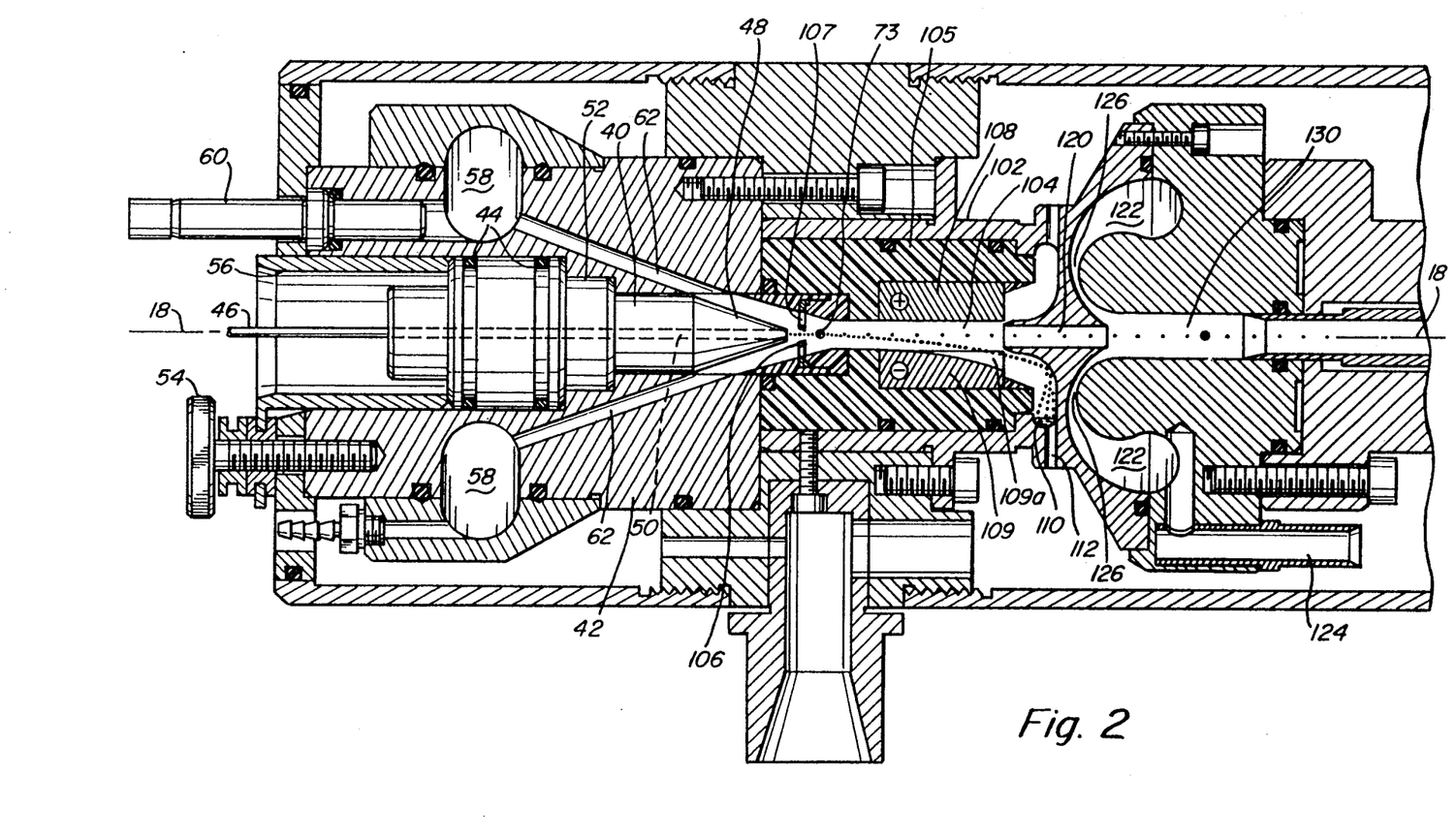
FIG. 2 is a cross-sectional view of the droplet generator and the drop-on-demand unit used in the non-volatile residue system of FIGS. 1A and 1B.

The droplet generator 14 is shown in FIG. 2. A droplet generator body 40 is mounted in a housing 42 with O-rings 44. The O-rings 44 permit vibration of droplet generator body 40 relative to housing 42. A tube 46 is connected to one end of droplet generator body 40 from micropump 10 (FIG. 1A). The tubing between the process line and the droplet generator 14 has a small diameter, typically on the order of about 0.030 inch, to reduce the dead volume of the sample liquid in the system. The droplet generator body 40 has a generally cylindrical shape with a tapered nozzle tip 48. A central passage 50 extends along the central axis of droplet generator body 40 from the inlet end connected to tube 46 to nozzle tip 48. The passage 50 typically has a diameter of about 0.030 to 0.060 inch. A piezoelectric crystal 52 is mounted circumferentially around the central passage 50. The piezoelectric crystal 52, when energized by an appropriate AC electrical signal, produces vibration of droplet generator body 40 along longitudinal axis 18. The vibration of droplet generator body 40 causes droplets to be emitted from tip 48 at the frequency of the energizing signal applied to piezoelectric crystal 52. The energizing signal for the piezoelectric crystal 52 is preferably a sine wave or a sawtooth wave at the desired droplet frequency. As discussed below, the droplet size can be controlled by varying the vibration frequency of piezoelectric crystal 52.

It has been found that the diameter of droplets emitted through an orifice at the end of nozzle tip 48 is approximately twice the diameter of the orifice. Thus, a nozzle tip 48 having an orifice diameter of 50 micrometers is required to generate droplets having a diameter of 100 micrometers. The droplet generator body 40 is easily replaceable in the system of the present invention by removing thumb screws 54 and a retainer 56. Thus, droplet generator bodies with different nozzle tips 48 can be utilized in the system. For example, interchangeable nozzle tips 48 with orifice diameters of 25, 50 and 100 micrometers produce droplet diameters of 50, 100 and 200 micrometers, respectively. The selection of droplet size in a range between about 55 micrometers and 150 micrometers is a tradeoff between competing factors. Droplets larger than the selected range are likely to be unstable and may break apart during transport through the system, thereby causing measurement errors. Extremely small droplets are stable but produce such small impurity particles after drying that measurement is not feasible with presently available equipment.

The droplet generator 14 further includes means for providing a flow of air in the region of nozzle tip 48 where the droplet stream is emitted. The housing 42 includes an annular manifold 58 connected through a conduit 60 to a source of low pressure air. Air passages 62 extend from manifold 58 to the region of nozzle tip 48. In a preferred embodiment, eight passages 62 are equally-spaced around nozzle 40. The passages 62 are inclined at an angle of 20° with respect to the longitudinal axis 18 of nozzle 40 and have a length-to-diameter ratio of at least 20:1. In a preferred embodiment, the passages 62 have a diameter of 0.090 to 0.125 inch. The passages 62 produce a converging air flow just beyond nozzle tip 48. In a preferred embodiment, a small portion of the main transport air is introduced through passages 62, and the main transport air is introduced farther downstream, as described below. Based on droplet size and droplet rate, approximately 15% of the main transport air is introduced through passages 62.

It has been found that variations in flow rate through droplet generator 14 caused by micropump 10 result in variations in droplet size. In accordance with a feature of the invention, the micropump 10 comprises a piezoelectric pump operated at a frequency that is much higher than the rate of droplet generation. Thus, for example, when droplets are generated at 10,000 droplets per second, the micropump 10 is driven at a frequency of 100KHz. With this arrangement, any variations in flow rate have a time scale that is much shorter than the droplet generation rate. Preferably, the micropump 10 is driven at a fixed frequency that is much higher than the highest droplet generation rate. Any other constant flow, minute pulsation pump system can be utilized with the non-volatile residue system, if droplet size stability is insured.

Figure 3:
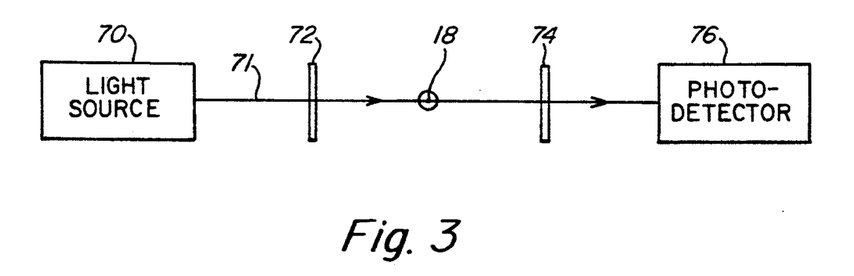
FIG. 3 is a schematic diagram of a first embodiment of the droplet inspection optics used in the non-volatile residue system of FIGS. 1A and 1B.

The droplet inspection unit 20 is used to measure sizes and, in some cases, shapes of the droplets generated by droplet generator 14. Since the volume concentration of impurities in a droplet is a function of the relative sizes of the particle and the droplet, any uncontrolled variation in droplet size introduces errors into the measurement of impurity volume concentration. A first embodiment of the droplet inspection unit 20, as viewed along axis 18 of the non-volatile residue system, is shown in FIG. 3. A light source 70, such as a laser diode, light-emitting diode or any other suitable light source, directs a light beam 71 through a lens 72 at the stream of droplets traveling along axis 18 (perpendicular to the plane of FIG. 3). The droplet inspection unit 20 preferably inspects the droplet stream at a point 73 (FIG. 2) along axis 18 that is about 0.25 inch downstream from nozzle tip 48. The lens 72 focuses the light on the droplet stream. The light transmitted through the droplet stream is focused by a lens 74 on a photodiode 76. When a droplet passes through the light beam 71, it causes a variation in the light received by photodiode 76 and a variation in the output electrical signal from photodiode 76. The amplitude of the signal resulting from a droplet passing through the light beam 71 is a measure of the droplet diameter. The droplet inspection system illustrated in FIG. 3 provides a droplet measurement accuracy of about 1% or better for spherical drops.

Figure 4:
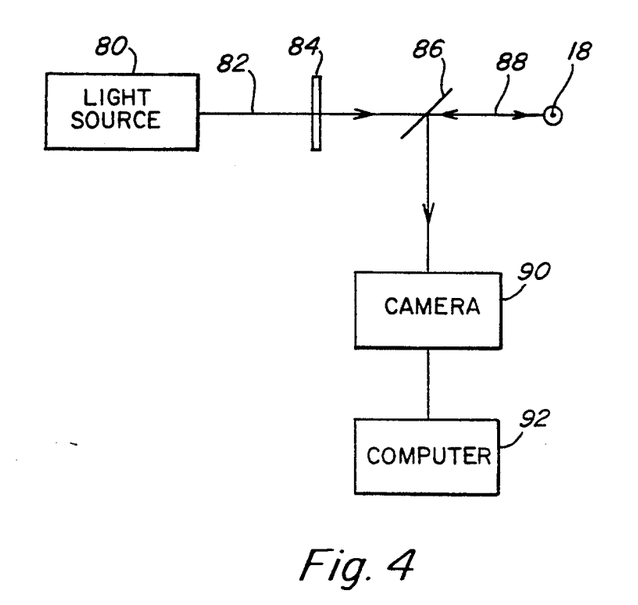
FIG. 4 is a schematic diagram of a second embodiment of the droplet inspection optics used in the non-volatile system of FIGS. 1A and 1B.

A second embodiment of the droplet inspection unit 20 is shown in FIG. 4. A light source 80, such as a laser diode or a light-emitting diode, directs a light beam 82 through a focusing lens 84 and a beam splitter 86 to a stream of droplets traveling along axis 18 (perpendicular to the plane of FIG. 4). The droplet stream is preferably inspected at point 73 shown in FIG. 2. Light is reflected from the individual droplets along a path 88 to beam splitter 86. The beam splitter 86 redirects the reflected light to a camera 90, which can be a charge-coupled device (CCD) video camera. The camera 90 obtains an image of the droplets on axis 18. The image is digitized and coupled through a suitable interface to a computer 92. The image of the droplets is analyzed by computer 92 using known shape analysis techniques, including least squares analysis, to determine the size, shape and volume of each droplet. A suitable shape analysis program is publicly available. The droplet inspection system shown in FIG. 4 is capable of measuring the droplets with an accuracy of 0.1% or better.

In accordance with an important feature of the present invention, the droplet inspection unit 20 is used to control the droplet generator 14 so as to provide droplets of uniform diameter. The droplet diameter is controlled by varying the frequency of the signal that energizes the piezoelectric crystal 52 in the droplet generator 14. Assume for example, that the desired droplet diameter is 100 micrometers. When the droplet inspection unit 20 measures an actual droplet diameter smaller than 100 micrometers, the frequency of the energizing signal applied to piezoelectric crystal 52 is decreased so as to increase the droplet diameter to 100 micrometers. Similarly, when the measured droplet diameter is larger than the desired diameter, the energizing signal for piezoelectric crystal 52 is increased in frequency. A feedback unit 16 (FIG. 1A) is used to maintain a constant droplet diameter by controlling the droplet rate. Feedback techniques for controlling the frequency of a signal generator are known in the art. The droplet inspection unit 20 and the feedback unit 16 can compensate for system variations, such as buildup of deposits in the droplet generator nozzle tip 48, variations in liquid flow rate and any other variations which cause the droplet diameter to vary.

As discussed above, a droplet generation rate of approximately 10,000 droplets per second produces droplets of the desired diameter for analysis at a relatively rapid flow rate from the process line or slipstream. However, it has been found that as the droplets pass through the heat exchanger 24 and are evaporated, two droplets sometimes agglomerate into a single large droplet. The large droplet may subsequently break apart into droplets of unequal size. Such droplets produce erroneous readings from the particle sizer 30 because the measured particles are derived from droplets of unknown diameter. The reason for droplet agglomeration is related to the drying process in the heat exchanger 24. As the droplets pass through the heat exchanger and the connecting tube to the particle sizer 30, the droplets evaporate and leave a vapor wake behind them. The volume of vapor from the evaporated droplets increases with distance along the heat exchanger and drying tube and causes a back pressure. The back pressure can cause a droplet to slow down sufficiently that it contacts a droplet behind it in the droplet stream. When this occurs, the droplets agglomerate and form a single larger droplet, as stated above.

The drop-on-demand unit 22 removes selected droplets from the droplet stream. Thus, for example, the drop-on-demand unit 22 may allow one of every 20 droplets to pass through the remainder of the system. In this instance, the spacing between droplets is increased by a factor of 20, thereby effectively eliminating the problems of droplet agglomeration and vapor loading in the heat exchanger 24. The fraction of droplets that are allowed to pass through the system is controllable.

The drop-on-demand unit 22 is shown in FIG. 2. A housing 102 includes a central passage 104 on axis 18. The principal components of the drop-on-demand unit 22 are a charging electrode 106 and deflection electrodes 108 and 109. Droplets are removed from the droplet stream by charging them with an electrical charge and then deflecting the charged droplets from the droplet stream using an electric field. A droplet is allowed to pass through the drop-on-demand unit 22 by not applying an electrical charge to the droplet. The uncharged droplet travels through the electric field without deflection.

Figure 5:
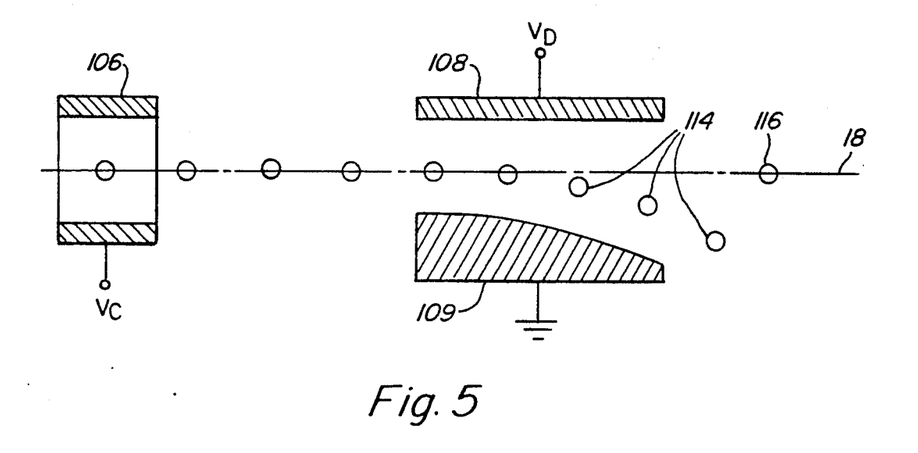
FIG. 5 is a schematic diagram illustrating operation of the drop-on-demand unit of FIG. 4.
Figure 6:
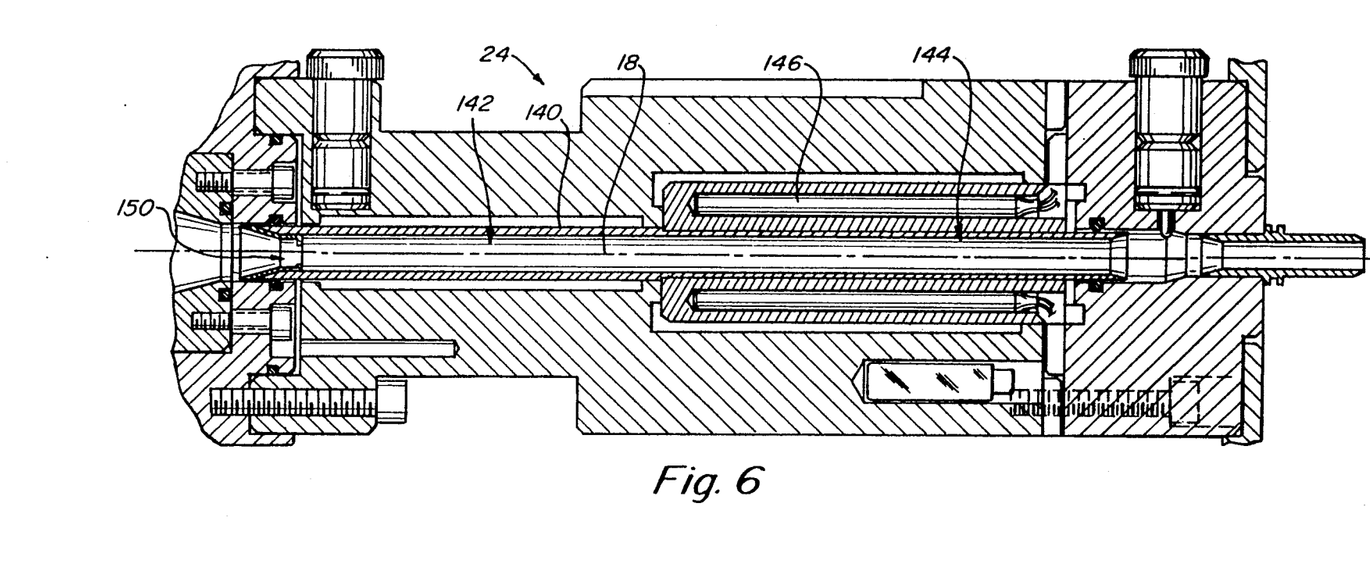
FIG. 6 is a cross-sectional view of the heat exchanger used in the non-volatile residue system of FIGS. 1A and 1B.
Figure 7:
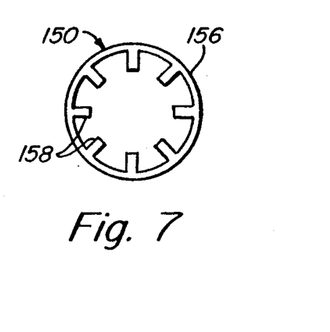
FIG. 7 is an end view of the vortex ring used at the entrance to the heat exchanger of FIG. 6.
Figure 8:
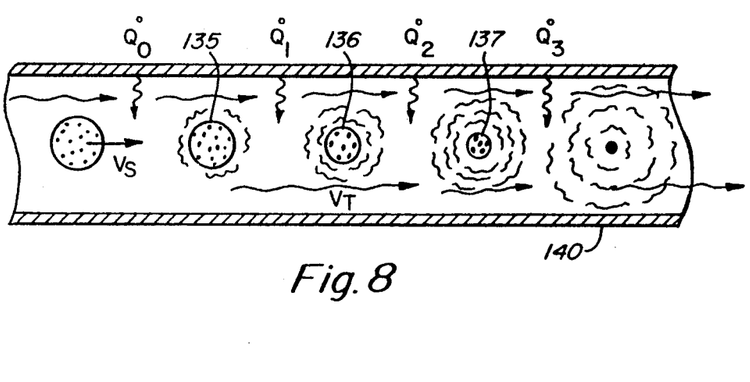
FIG. 8 is a schematic diagram that illustrates droplet drying in the heat exchanger of FIG. 6.

Operation of the drop-on-demand unit 22 is illustrated schematically in FIG. 5. Droplets 114 are charged by charging electrode 106 and are deflected from axis 18 by deflection electrodes 108 and 109. Droplet 116 is not charged by electrode 106 and continues along axis 18 without deflection by electrodes 108 and 109.

The charging electrode 106 comprises a conductive ring typically having a length of about 0.030 inch and a diameter of about 0.090 inch. The charging electrode 106 is supported in front of nozzle tip 48 by radial spokes 107 which minimize disturbance of the air flow from passages 62. The charging electrode 106 is electrically insulated from housing 102 by an insulator 105. A charging voltage in the range of about 50 volts to 150 volts is applied to charging electrode 106 in order to charge the droplets. The charging voltage is pulsed to zero volts to permit passage of an uncharged droplet. The pulsing of charging electrode 106 to zero volts to permit passage of uncharged droplets is synchronized to the voltage that drives the piezoelectric crystal 52 in the droplet generator 14, with appropriate delay. It will be understood that one droplet is produced by droplet generator 14 for each cycle of the voltage applied to piezoelectric crystal 52.

The deflection electrodes 108 and 109 comprise plate electrodes having typical dimensions of about 0.75 inch long by 0.25 inch wide. The deflection electrodes 108 and 109 are also insulated from housing 102 by insulator 105. The electrode 109 preferably includes a contoured groove 109a which provides a passage for deflected droplets. The electrode 109 is typically at ground potential. A voltage on the order of 200 to 800 volts is applied to deflection electrode 108, causing an electric field in the portion of passage 104 between electrode 108 and electrode 109. The charged droplets are deflected by deflection electrodes 108 and 109 into a collection reservoir 110. The collected droplets are removed from the system through a drain tube 112. Uncharged droplets travel past electrodes 108 and 109 without deflection and continue along axis 18.

In the above example where one out of every 20 droplets is allowed to pass through the system by the drop-on-demand unit 22, the charging electrode 106 is pulsed to zero volts during the passage of a first droplet, and a charging voltage is applied to electrode 106 during the passage of droplets 2 through 20. The first uncharged droplet travels through passage 104 without deflection and continues through the remainder of the system for analysis. Droplets 2 through 20 are deflected into collection reservoir 110. This process is repeated continuously so that the droplet rate is reduced by a factor of 20, and the droplet spacing along axis 18 is increased by a factor of 20. It will be understood that any desired fraction of droplets can be allowed to pass through the drop-on-demand unit 22.

The drop-on-demand unit 22 includes an eduction passage 120 downstream of deflection electrodes 108 and 109. As the droplets emerge from passage 104 through eduction passage 120, they are entrained in the merging transport air stream. The housing 102 is provided with an annular manifold 122 having a conduit 124 for connection to a source of low pressure air. Air is supplied to manifold 122 at a flow rate of about 6 liters per minute. An annular air passage 126 extends from manifold 122 to a region 130 downstream from eduction passage 120. Air flowing through passage 126 merges on axis 18 beyond eduction passage 120. Droplets emerging from eduction passage 120 are entrained in the air and are transported through the heater exchanger 24.

The heat exchanger 24 is shown in FIG. 6. A heat exchanger tube 140 is fabricated of a thermally conductive material such as aluminum or stainless steel. The tube 140 has a length of about 6 to 7 inches and an inside diameter of about 0.25 inch. The inside diameter is a tradeoff between efficient thermal transfer to the droplet stream and the required transport velocity to prevent the droplets from contacting the tube walls as a result of gravitational forces. The heat exchanger 24 includes a first upstream section 142 and a second downstream section 144. The downstream section 144 includes a heater 146 around the heat exchange tube 140. The heater 146 comprises four resistively-heated rods that are equally spaced around heat exchanger tube 140. Each rod has a rating of 50 watts, and the heater 146 has a total rating of 200 watts. A heater control permits control of the temperature of the transport gas passing through tube 140 in a range of 0° to 600° F. The upstream section 142 of heat exchanger 24 is heated by conduction from heater 146. The heat exchanger 24 further includes a vortex shedder 150 at the inlet to heat exchanger tube 140 for improving heat transfer to the droplet stream as described below. The vortex shedder is removable when enhanced heat transfer is not required.

The heat exchanger 24 produces a temperature profile within heat exchanger tube 140 for effective droplet drying and particle formation. The heat exchanger should produce complete drying of each droplet before the droplet reaches particle sizer 30. The gradual evaporation of droplets 135, 136, 137, etc. to form a particle and a vapor wake is shown schematically in FIG. 8. The droplets should be dried in such a way that impurities in each droplet coalesce to form a single particle. It has been found that this can be accomplished by heating the droplets without boiling. In particular, the heat exchanger 24 provides a gradual increase in temperature in upstream section 142 and a constant temperature in downstream section 144 adjacent to heater 146. The upstream section 142 has a log mean temperature profile as a result of conduction from heater 146. It has been found that the best results are obtained when the heater 146 produces a temperature in the transport gas in downstream section 144 that is equal to the boiling temperature of the liquid in the sample. The temperature is controlled to within about one-half degree of the desired boiling temperature.

In order to transport droplets in the size range of 55 to 150 micrometers, laminar flow has been found desirable. In laminar flow, the velocity profile within heat exchanger tube 140 is parabolic, with a maximum velocity at the center and zero velocity at the walls of tube 140. It has been found that a transport velocity of about 7 feet per second is suitable for transport of droplets of most liquids to be analyzed. The selected transport velocity is a tradeoff between competing factors. At low velocities, the droplets may contact the walls of tube 140 as a result of gravity. At high velocities, the droplets can break apart.

The vortex shedder 150 is used enhance transfer of heat to the droplet stream within heat exchanger 24. The purpose of the vortex shedder 150 is to produce vortices in a region close to the wall of heat exchanger tube 140. The vortices create a turbulent region which enhances heat transfer to the transport gas and thus to the droplet stream. In a preferred embodiment shown in FIG. 7, the vortex shedder 150 includes a generally cylindrical wall 156 having a plurality of inwardly-extending posts 158. The posts 158 cause regions of turbulence along the wall of heat exchanger tube 140. In another embodiment of the vortex ring, the inwardly-extending posts 158 are replaced with an inwardly-extending annular rib. It has been found that the regions of turbulence caused by vortex shedder 150 continue throughout a major portion of the length of heat exchanger 24. Tests have shown that the transport gas stream within the heater exchanger 24 reaches a desired temperature using a vortex shedder in less than the time required when the vortex shedder is not utilized.

As indicated above, the droplets are only partially evaporated when they reach the downstream end of the heat exchanger 24. At this point in the system, the transport gas is at the boiling temperature of the liquid in the droplets. The tube between the heat exchanger 24 and particle sizer 30 (which can optionally include charge neutralizer 28) typically has a length of about 18 inches. As the transport gas passes through the tube to particle sizer 30, it gradually cools and the droplets continue to evaporate. At the entrance to particle sizer 30, the transport gas has a temperature of about 80° F. and the droplets have completely dried, leaving a non-volatile residue particle representative of the impurities in the liquid.

As indicated above, the particle sizer 30 utilizes a time-of-flight measurement technique to determine particle size. Briefly, the particles travel through two spaced-apart laser beams. The laser beams are detected by photomultiplier detectors. Particles passing through the laser beams cause successive output pulses on the two photomultipliers. The time required for the particles to travel between the two laser beams is a known function of particle size. The output signals from the photomultipliers are analyzed to determine particle sizes. The volume concentration of impurities in the liquid sample is given by the following equation $$C=(d/D)^3$$

where C is the volume concentration of the impurities, d is the diameter of the non-volatile residue particle, and D is the diameter of the droplet.

The non-volatile residue system described above can be used to identify organic impurities in the liquid sample. Such organic impurities typically comprise oil that may be introduced into the liquid from valves or other system components. In order to identify organic impurities, the temperature of heater 146 in the heat exchanger 24 is raised to a temperature on the order of 210° F. or greater. This temperature is sufficient to cause evaporation not only of the liquid portion of the droplets but also of organic impurities. The particle size at the elevated temperature of heat exchanger 24 is measured. Then, the measurement is repeated with the heat exchanger at the normal boiling temperature for that liquid. If a reduction in particle size is noted at the higher temperature, it is assumed that the liquid sample contains organic impurities which evaporated from the droplets at the elevated temperature and caused a reduction in particle size. If the particle size is approximately the same at both temperatures, the impurities are identified as inorganic salts which do not evaporate at the elevated temperature of heat exchanger 24.

The droplet generator 14 can be provided with a continuously variable orifice to control droplet diameter. The droplet diameter is controlled by varying the inside diameter of the orifice at the outlet of nozzle tip 48. The orifice diameter can be controlled by a variety of techniques, including a toroidal bladder that is inflatable, an iris, or any other suitable technique for varying the orifice diameter. One advantage of a variable diameter orifice is that it can be opened to maximum diameter so as to flush the system and thereby remove any contaminant deposits or clogging bodies.

The bias voltage on the deflection electrode 108 in the drop-on-demand unit 22 is typically maintained at a constant voltage for deflection of charged droplets. The bias voltage can be adjusted for control of the trajectory of droplets through the system. That is, the bias voltage is adjusted so that the droplets which are not deflected by electrode 108 are accurately aligned on axis 18. The uncharged droplets that are allowed to pass through the drop-on-demand unit 22 have a small electrical charge that permits them to be slightly deflected by electrode 108.

Light source 80 shown in FIG. 4 is located on the same side of the droplet stream as camera 90. Alternatively, the light source 80 and camera 90 can be located on opposite sides of the droplet stream in a manner similar to the configuration shown in FIG. 3.

While there have been shown and described what are at present considered the preferred embodiments of the present invention, it will be obvious to those skilled in the art that various changes and modifications may be made therein without departing from the scope of the invention as defined by the appended claims.

What is claimed is:

1. A system for monitoring impurities in a liquid comprising:
   means for generating a stream of droplets of the liquid;
   means for removing selected droplets from the stream of droplets to provide a desired spacing between droplets in the stream of droplets;
   means for drying said stream of droplets after removal of said selected droplets to provide non-volatile residue particles; and
   means for analyzing said non-volatile residue particles to provide an indication of the impurities in said liquid.

2. A system as defined in claim 1 wherein said means for removing selected droplets includes means for charging said selected droplets with an electrical charge to provide charged droplets and means for deflecting said charged droplets from said stream of droplets.

3. A system as defined in claim 2 wherein said means for charging comprises a charging electrode positioned adjacent to said stream of droplets and means for applying a charging voltage to said charging electrode.

4. A system as defined in claim 3 wherein said means for deflecting said charged droplets comprises deflection electrodes positioned downstream of said charging electrode and means for applying a deflection voltage between said deflection electrodes.

5. A system as defined in claim 3 wherein the means for applying a charging voltage includes means for pulsing said charging voltage to zero volts to permit passage of non-selected droplets.

6. A system as defined in claim 1 wherein said means for removing selected droplets includes means for periodically removing a predetermined fraction of said droplets so as to increase a spacing between said droplets in said stream of droplets.

7. A system as defined in claim 2 wherein said means for removing selected droplets includes a collection reservoir for receiving droplets removed from said stream of droplets.

8. A system for monitoring impurities in a liquid comprising:
   means for generating a stream of droplets of the liquid, including a nozzle for emitting said stream of droplets and means for vibrating said nozzle at a droplet rate;
   means for inspecting said stream of droplets and determining a: droplet diameter;
   feedback means responsive to said droplet diameter for varying the droplet rate of said vibrating means when said droplet diameter is outside a predetermined range such that said droplet diameter is maintained within said predetermined range;
   means for drying said droplets to provide non-volatile residue particles; and
   means for analyzing said non-volatile residue particles to provide an indication of the impurities in said liquid.

9. A system as defined in claim 8 wherein said means for inspecting said stream of droplets comprises means for illuminating said stream of droplets with a light beam and means for detecting variations in said light beam caused by said droplets.

10. A system as defined in claim 9 wherein said means for detecting comprises a photodiode.

11. A system as defined in claim 8 wherein said means for inspecting said stream of droplets comprises means for illuminating said stream of droplets, a camera for obtaining an image of said stream of droplets and means for analyzing said image to determine the diameter of said droplets.

12. A system as defined in claim 8 wherein said means for vibrating said nozzle comprises a piezoelectric crystal attached to said nozzle and means for energizing said piezoelectric crystal at said droplet rate.

13. A system as defined in claim 12 wherein said droplet rate is in a range of about 6,000 droplets per second to 12,000 droplets per second.

14. A system as defined in claim 8 wherein said droplet size is controlled at a selected diameter in a range of about 55 micrometers to 155 micrometers.

15. A system as defined in claim 8 further including a piezoelectric micropump for supplying said liquid to said means for generating a stream of droplets, said piezoelectric micropump being energized at a frequency that is much higher than said droplet rate.

16. A system as defined in claim 15 wherein said piezoelectric micropump provides said liquid to said means for generating a stream of droplets at a flow rate in the range of about 0.3 to 0.6 cubic centimeters per minute.

17. A system for monitoring impurities in a liquid comprising:
means for generating a stream of droplets of the liquid;
means for drying said droplets to provide non-volatile residue particles, said means for drying said droplets comprising a heat exchanger including a first section for gradually heating said droplets to a predetermined temperature and a second section for maintaining said droplets at said predetermined temperature; and
means for analyzing said non-volatile residue particles to provide an indication of the impurities in said liquid.

18. A system as defined in claim 17 wherein said heat exchanger includes a thermally-conductive heat exchanger tube extending through said first and second sections and a heater disposed around said heat exchanger tube in said second section.

19. A system as defined in claim 17 wherein said predetermined temperature is about the boiling temperature of said liquid.

20. A system as defined in claim 17 wherein said first section has a log mean temperature profile and said second section has a constant temperature profile.

21. A system as defined in claim 18 further including a vortex shedder at an inlet of said heat exchanger tube for producing turbulence along the inside wall of said heat exchanger tube to thereby improve-heat transfer to said stream of droplets.

22. A system as defined in claim 21 wherein said vortex shedder comprises a generally cylindrical tube having a plurality of inwardly-extending posts.

23. A system for monitoring impurities in a liquid comprising:
means for generating a stream of droplets of the liquid;
means for drying said droplets to provide non-volatile residue particles;
means for measuring the diameters of said non-volatile residue particles to provide an indication of the volume concentration of impurities in said liquid; and
means for analyzing the composition of said non-volatile residue particles in real time to provide an indication of the composition of the impurities in said liquid.

24. A system as defined in claim 23 wherein said means for analyzing the composition of said non-volatile residue particles comprises a spectrometer.

25. A method for monitoring impurities in a liquid comprising the steps of:
generating a stream of droplets of the liquid;
removing selected droplets from the stream of droplets to provide a desired spacing between droplets in the stream of droplets;
drying the stream of droplets after removal of the selected droplets to provide non-volatile residue particles; and
analyzing the non-volatile residue particles to provide an indication of the impurities in the liquid.

26. A method as defined in claim 25 wherein the step of removing selected droplets includes charging the selected droplets with an electrical charge to provide charged droplets and deflecting the charged droplets from the stream of droplets with an electric field.

27. A method as defined in claim 25 wherein the step of removing selected droplets includes periodically removing a predetermined fraction of the droplets so as to increase a spacing between the droplets in the stream of droplets.

28. A method for monitoring impurities in a liquid comprising the steps of:
generating a stream of droplets of the liquid by vibrating a nozzle at a droplet rate so as to emit the stream of droplets;
inspecting the stream of droplets and determining a droplet diameter;
varying the rate of vibrating the nozzle in response to the determined droplet diameter when the droplet diameter is outside a predetermined range such that the droplet diameter is maintained within the predetermined range;
drying the droplets to provide non-volatile residue particles; and
analyzing the non-volatile residue particles to provide an indication of the impurities in the liquid.

29. A method as defined in claim 8 wherein the step of inspecting the stream of droplets includes obtaining an image of the stream of droplets with a camera and analyzing image to determine the diameter of the droplets.

30. A method for monitoring impurities in a liquid comprising the steps of:
generating a stream of droplets of the liquid;
drying the droplets to provide non-volatile residue particles, the step of drying the droplets including gradually heating the droplets to the boiling temperature of the liquid and maintaining the droplets at the boiling temperature of the liquid; and
analyzing the non-volatile residue particles to provide an indication of the impurities in the liquid.

31. A method for monitoring impurities in a liquid comprising the steps of:

generating a stream of droplets of the liquid;
drying the droplets to provide non-volatile residue particles;
measuring the diameters of the non-volatile residue particles to provide an indication of the volume concentration of impurities in the liquid; and
analyzing the composition of the non-volatile residue particles in real time to provide an indication of the composition of the impurities in the liquid.

32. A system as defined in claim 21 wherein said vortex shedder comprises a generally cylindrical tube having an inwardly extending annular rib.

* * * * *